United States Patent
Walls

(10) Patent No.: US 8,673,018 B2
(45) Date of Patent: Mar. 18, 2014

(54) METHODS OF USING WATER-SOLUBLE INORGANIC COMPOUNDS FOR IMPLANTS

(75) Inventor: James A. Walls, Bethany, CT (US)

(73) Assignee: AMx Tek LLC, Bethany, CT (US)

(*) Notice: Subject to any disclaimer, the term of this patent is extended or adjusted under 35 U.S.C. 154(b) by 219 days.

(21) Appl. No.: 13/019,265

(22) Filed: Feb. 1, 2011

(65) Prior Publication Data
US 2011/0196502 A1 Aug. 11, 2011

Related U.S. Application Data

(60) Provisional application No. 61/301,698, filed on Feb. 5, 2010.

(51) Int. Cl.
*A61F 2/28* (2006.01)

(52) U.S. Cl.
USPC ........................................ 623/23.57

(58) Field of Classification Search
USPC ........................................ 623/23.57
See application file for complete search history.

(56) References Cited

U.S. PATENT DOCUMENTS

| | | |
|---|---|---|
| 3,808,606 A | 5/1974 | Tronzo |
| 3,855,638 A | 12/1974 | Pilliar |
| 4,146,936 A | 4/1979 | Aoyagi et al. |
| 4,746,532 A | 5/1988 | Suzuki et al. |
| 4,813,965 A | 3/1989 | Roberts |
| 4,938,409 A | 7/1990 | Roberts |
| 5,049,139 A | 9/1991 | Gilchrist |
| 5,470,585 A | 11/1995 | Gilchrist |
| 5,797,898 A | 8/1998 | Santini, Jr. et al. |
| 5,800,553 A * | 9/1998 | Albrektsson et al. ........ 623/22.4 |
| 5,876,446 A | 3/1999 | Agrawal et al. |
| 5,914,356 A | 6/1999 | Erbe |
| 5,947,893 A | 9/1999 | Agrawal et al. |
| 6,692,532 B1 | 2/2004 | Healy et al. |
| 6,709,379 B1 | 3/2004 | Brandau et al. |
| 6,736,849 B2 | 5/2004 | Li et al. |
| 7,122,057 B2 * | 10/2006 | Beam et al. ................ 623/23.51 |

(Continued)

FOREIGN PATENT DOCUMENTS

| | | |
|---|---|---|
| EP | 1911468 A2 | 4/2008 |
| WO | WO-2006031965 A3 | 3/2006 |

(Continued)

OTHER PUBLICATIONS

Piza et al., Hydroxyapatite-coated external-fixation pins, J of Bone and Joint Surgery, 2004, 86-B: 892-7, GB.

(Continued)

*Primary Examiner* — Bruce E Snow
*Assistant Examiner* — Melissa Hoban
(74) *Attorney, Agent, or Firm* — Douglas E. Denninger

(57) ABSTRACT

A method for controlling generation of biologically desirable voids in a composition placed in proximity to bone or other tissue in a patient by selecting at least one water-soluble inorganic material having a desired particle size and solubility, and mixing the water-soluble inorganic material with at least one poorly-water-soluble or biodegradable matrix material. The matrix material, after it is mixed with the water-soluble inorganic material, is placed into the patient in proximity to tissue so that the water-soluble inorganic material dissolves at a predetermined rate to generate biologically desirable voids in the matrix material into which bone or other tissue can then grow.

45 Claims, 4 Drawing Sheets

(56) References Cited

U.S. PATENT DOCUMENTS

| | | | |
|---|---|---|---|
| 7,354,605 | B2 | 4/2008 | Trogolo et al. |
| 7,368,065 | B2 | 5/2008 | Yang et al. |
| 7,531,005 | B1 | 5/2009 | Healy et al. |
| 7,595,355 | B2 | 9/2009 | Trogolo |
| 2003/0171820 | A1 | 9/2003 | Wilshaw et al. |
| 2005/0221259 | A1 | 10/2005 | Anderson |
| 2006/0093646 | A1 | 5/2006 | Cima et al. |
| 2006/0198863 | A1 | 9/2006 | DePaula |
| 2006/0292199 | A1 | 12/2006 | Kuhn et al. |
| 2007/0016163 | A1 | 1/2007 | Santini, Jr. et al. |
| 2007/0287027 | A1 | 12/2007 | Justin et al. |
| 2008/0038534 | A1 | 2/2008 | Zenati et al. |
| 2008/0156232 | A1 | 7/2008 | Crudden et al. |
| 2008/0172011 | A1 | 7/2008 | Heroux et al. |
| 2008/0187571 | A1 | 8/2008 | Clineff et al. |
| 2008/0213336 | A1 | 9/2008 | Kuhn et al. |
| 2008/0226688 | A1 | 9/2008 | DePaula |
| 2008/0262629 | A1 * | 10/2008 | Fonte .................. 623/23.15 |
| 2008/0268011 | A1 | 10/2008 | Goldmann et al. |
| 2009/0010981 | A1 | 1/2009 | Bechert et al. |
| 2009/0112332 | A1 | 4/2009 | Shelokov |
| 2009/0198344 | A1 | 8/2009 | Prentice et al. |
| 2009/0208428 | A1 | 8/2009 | Hill et al. |
| 2010/0055019 | A1 | 3/2010 | Day et al. |
| 2010/0168798 | A1 | 7/2010 | Clineff et al. |
| 2011/0070284 | A1 | 3/2011 | Depaula et al. |

FOREIGN PATENT DOCUMENTS

| | | | | |
|---|---|---|---|---|
| WO | WO 2008/049242 | A1 * | 5/2008 | ............ A61L 27/48 |
| WO | WO-2009062671 | A2 | 5/2009 | |
| WO | WO-2009062671 | A3 | 5/2009 | |
| WO | WO-2009148880 | A3 | 12/2009 | |
| WO | PCT/US2011/023784 | | 10/2011 | |

OTHER PUBLICATIONS

Coester et al., The Effects of Silver Coated External Fixation Pins, Iowa Orthopedic J, 2006, 26:48-53, U. Iowa, US.

Barradas, Molecular analysis of biomaterial-driven osteogenic differentiation of human mesenchymal stem cells, BioInterface 2011 Presentation, U. Twente, NL.

Kuhn, Bone Cements, Up-to-Date Comparison of Phys-Chem Properties, 2000, pp. 16, 27-28, 141-142, 253-256, Springer, DE.

Novabone, 510(k) Summary for PerioGlas-Bioglass Bone Graft Particulate, Feb. 3, 2004, K040278, FDA, US.

Pratten et al., In Vitro Attachment of S. epidermidis to Surgical Sutures, J. Biomaterials Applications, Jul. 2004, pp. 48-57, vol. 19, Sage Publ.

Cooper et al., Fiber-based tissue-engineered scaffold for ligament replacement, Biomaterials, 2005, pp. 1523-1532, vol. 26, Elsevier.

Lu et al., ACL regeneration using braided biodegradable scaffolds, Biomaterials, 2005, pp. 4805-4816, vol. 26, Elsevier.

Chen et al., 45S5 Bioglass-derived glass-ceramic scaffolds for bone tissue eng., Biomaterials, 2006, pp. 2414-2425, vol. 27, Elsevier.

Nanotherapeutics, 510(k) Summary for Origen DBM with Bioactive Glass, Feb. 16, 2007, K062459 FDA, US.

Freeman et al., Recent Advances in Ligament Tissue Eng., Recent Patents on Biomedical Eng, 2008, pp. 18-23, vol. 1 No. 1.

DiFusion Technologies Completes Successful Testing of Antimicrobial Spinal Implant, Jan. 26, 2009, Press Release, www.difusiontech.com.

Lischer et al., Silver Releasing Hydroxyapatite Coatings for Implant Apps, European Cells and Materials, 2010, p. 30, vol. 20 suppl. 1.

Morscher et al., Cementless Fixation of a Polyethylene Acetabular Component, The Cementless Fixation of Hip Endoprostheses, 1984, pp. 200-204, Springer-Verlag, DE.

Bellatone et al., Broad-Spectrum Bactericidal Activity of Ag-Doped Bioactive Glass, Antimicrob. Agents Chemother.,2002, pp. 1940-1945, v.46#6.

Nelson, The Current Status of Material Used for Depot Delivery of Drugs, Clinical Orthop. and Related Research, 2004, pp. 72-78, No. 427.

Tobler et al. Nanotech Silver Fights Microbes in Medical Devices, http://www.orioncoat.com/site/epage/62785_691.htm, May 2005, pp. 1-5.

Shi et al.,Antibacterial and mechanical properties of bone cement impregnated with chitosan nanoparticles, Biomaterials, 2006, pp. 2440-2449, v.27, Elsevier.

Ewald et al., Antimicrobial titanium/silver PVD coatings on titanium, BioMed. Eng. OnLine, Mar. 2006, pp. 1-10, V. 5:22.

Hetrick et al., Reducing implant-related infections: active release strategies, Chem. Soc. Rev., 2006, pp. 780-789, v. 35., Royal Soc. Chem.

Nuss et al., Biocompatibility Issues with Modern Implants in Bone, The Open Orthopaedics J., 2008, pp. 66-78, v.2.

Liao Juan et al, Deposition of silver nanoparticles on titanium surface for antimicrobial effect, Int'l J. Nanomed., 2010, pp. 261-267, v.5, Dove Medical Press.

Liao et al., Antibacterial titanium plate deposited by silver nanoparticles exhibits cell compatibility, Int'l J. of Nanomedicine, 2010, pp. 337-342, v.5, Dove Medical Press.

Gerhardt et al., Bioactive Glass and Glass-Ceramic Scaffolds for Bone Tissue Engineering, Materials, 2010, pp. 3867-3910, v. 3, doi:10.3390/ma3073867.

* cited by examiner

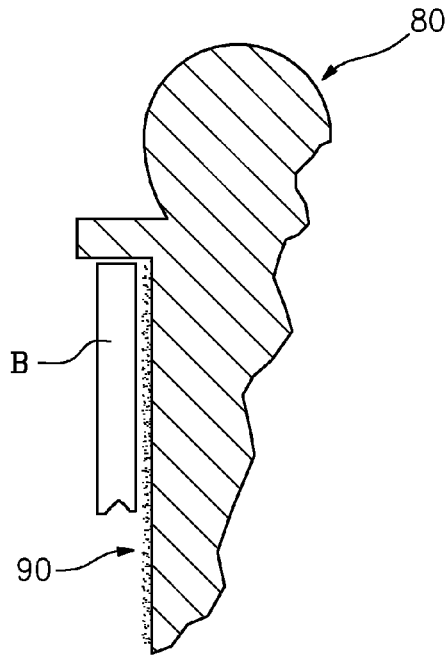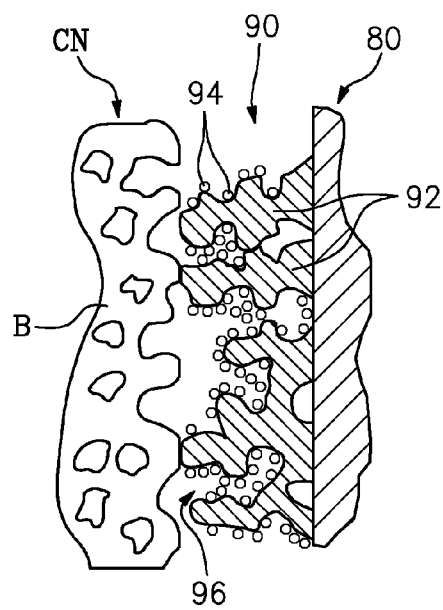
FIG. 5A  FIG. 5B
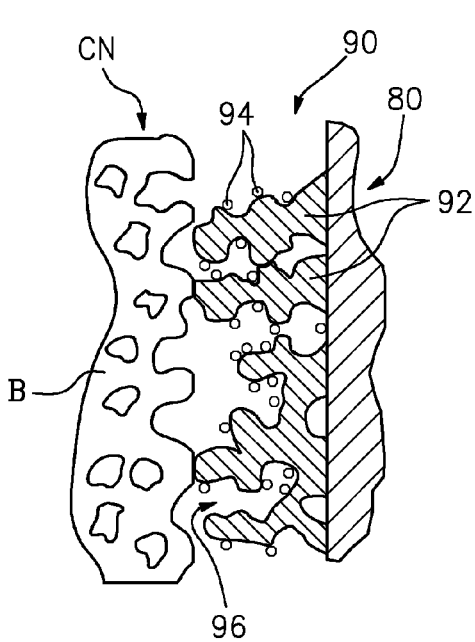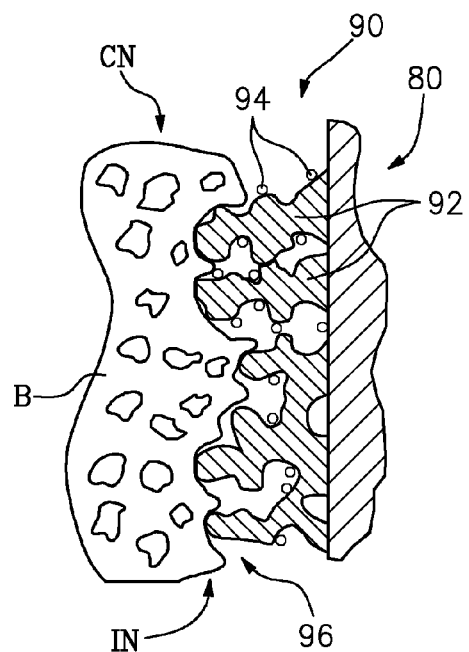
FIG. 5C  FIG. 5D

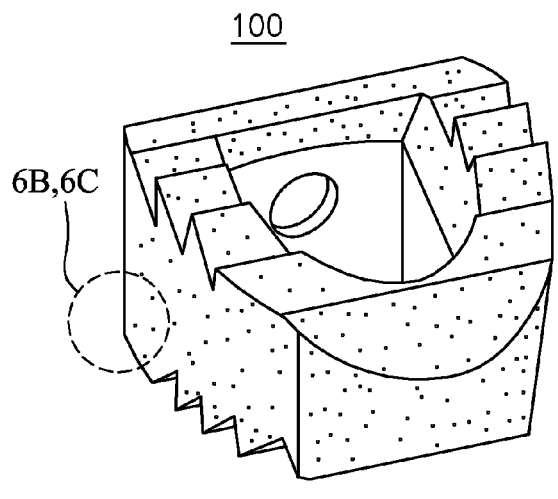
*FIG. 6A*
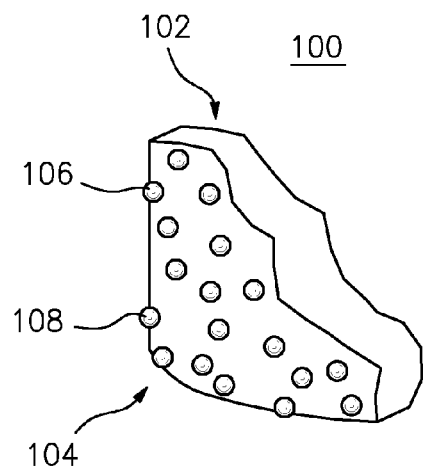
*FIG. 6B*
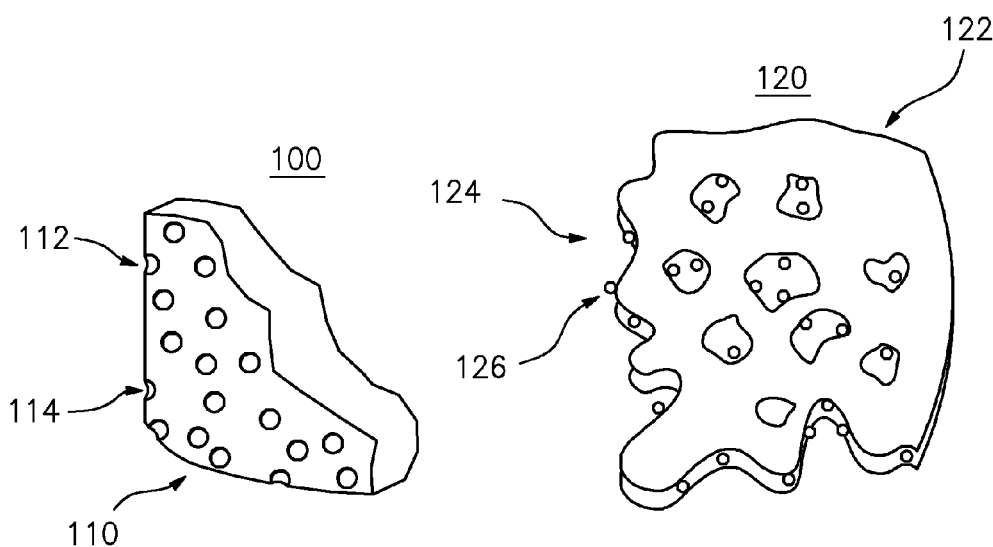
*FIG. 6C*     *FIG. 7*

METHODS OF USING WATER-SOLUBLE INORGANIC COMPOUNDS FOR IMPLANTS

CROSS-REFERENCE TO RELATED APPLICATION

This application claims priority to U.S. Provisional Application No. 61/301,698 filed 5 Feb. 2010.

FIELD OF THE INVENTION

The invention relates to methods of using mixtures having one or more types of water-soluble inorganic materials which dissolve in the presence of bodily fluids after implantation in a patient to generate biologically desirable voids within matrix materials, the voids preferably having therapeutically desirable patient benefits.

BACKGROUND OF THE INVENTION

Orthopaedic reconstruction and trauma repair often utilize metallic, polymeric, and biodegradable materials devices, as well as allograft and autograft tissues, for replacement, fixation and repair of patient bones and other tissues. Some such devices are implanted percutaneously and temporarily, including fixator pins, while other such devices are surgically implanted and intended for long-term repair, replacement, and/or reconstruction, such as bone plates, spinal and dental implants, and artificial joints.

There are a variety of metal implants that are secured within bone by allowing bone to grow into pores purposefully manufactured on the surface of the implants. Early bone implants formed of metal with metal particles sintered thereon to create metallic porous surfaces are described in U.S. Pat. No. 3,808,606 by Tronzo. Such metal particles are typically sintered onto the implants surface, although other techniques of particle bonding are known including brazing as disclosed in U.S. Pat. Nos. 4,813,965 and 4,938,409 by Roberts. Other implants use porous coatings made from ceramic materials and hydroxyapatite, to encourage bone attachment, as detailed in U.S. Pat. Nos. 4,146,936 and 4,746,532 by Aoyagi et al. and Suzuki et al., respectively.

A number of orthopaedic devices are designed to be fixated by impaction, such as intramedullary nails which are driven into the marrow of bones. Other orthopaedic implants, for example bone plates and spinal interbody cages, are typically fixated with threaded screws. Many conventional implant coatings cannot withstand the shear forces associated with such impaction or torque fixation techniques.

All surgeries carry inherent risk of infection. Once an implant becomes colonized by microorganisms and a microbial biofilm is formed, eradicating such infection by systemic antibiotics is extremely difficult. Often an infected implant must be surgically removed, referred to as revision surgery, and the surrounding tissue and bone are debrided and treated directly via antibiotic lavage. Sometimes a short-term "spacer" element is temporarily implanted to hold anatomical structures in place while the patient undergoes antibiotic therapy. Ultimately a new long-term device is implanted. The cost, morbidity and mortality associated with such surgical intervention can be significant.

Reducing the risk of infection, therefore, is highly desirable. Surgeons often treat implants directly and/or the implant surgical site directly with antibiotics at the time of surgery in an effort to prophylactically protect the device and kill microorganisms inadvertently introduced into the operative site during the surgical procedure. Trauma-induced bone fractures often involve wounds that penetrate the patient's skin, breaching the skin's protective barrier, creating "dirty" wounds, requiring external fixator pins to align and fixate bone fragments percutaneously for months following injury until such broken bones heal. In such circumstances, microorganisms introduced at the time of the fracture, as well as the patient's own microbial flora migrating down a percutaneous fixator pin tract, can infect the patient's own soft tissue and bone, causing osteomyelitis and/or other soft tissue and blood stream related infections.

Reservoirs within implantable devices have been provided for antibiotics and other bioactive agents such as described in U.S. Pat. No. 6,709,379 by Brandau et al., U.S. Patent Publication Nos. 2006/0093646 by Cima et al. and 2007/0016163 by Santini Jr. et al. Other types of infection resistant orthopaedic devices include the EBI X Fix Dynafix™ System with SC Bone Screws which employs silver as a biocide, manufactured by Electro-Biology Inc. of Parsippany, N.J., and OrthoGuard™ AB Antibacterial Sleeve containing the antibiotic gentamicin, from Smith & Nephew, Inc. of Memphis, Tenn. Silver ions absorbed into hydroxyapatite coatings on metal implants are disclosed in U.S. Patent Publication No. 2009/0198344 by Prentice et al.

Orthopaedic implants are often secured with bone cement such as PMMA (polymethylmethacrylate), which may contain one or more organic antibiotics, such as Zimmer Holding's Palacos® R+G bone cement containing gentamicin and Stryker Corporation's Simplex™ P containing tobramycin. Antibiotic bone cements are also disclosed by Kuhn et al. in U.S. Patent Publication Nos. 2006/0292199 and 2008/0213336. Kuhn et al. teach that most of the antibiotic should be released within the first 24 hours after implantation.

Antibiotics are organic substances produced by microorganisms that are antagonistic to the growth of other microorganisms. Today, many such antibiotics are synthetically derived. The antagonistic property of an antibiotic is somewhat microorganism-specific. Consequently, the biocidal effectiveness of any antibiotic is highly predicated upon selecting the appropriate antibiotic for the infecting pathogen. Kuhn et al. promote the use of gentamicin as a "broadly effective" antibiotic in the above-cited U.S. Patent Publications, yet microbes, such as E. coli, have demonstrated some resistance to gentamicin, as have other microorganisms to other antibiotics. Also, possible side effects of gentamicin include damage to kidneys and/or nerves, which can cause dizziness, numbness, muscle twitching or seizures. Moreover, gentamicin is not recommended for people having kidney disease, hearing loss or loss of balance due to ear problems, or having a neuromuscular disorder.

Heat generated during the porous coating process of metal implants, various implant sterilization processes, and the elevated polymerization temperatures of a thermoplastic material such as PMMA, each may have deleterious effects on antibiotics and other organic materials and organic bioactive agents. While U.S. Pat. Nos. 5,876,446 and 5,947,893 by Agrawal et al. teach the use of antibiotic-loaded biodegradable polymers as a coating means for porous implants, the process of imbibing the antibiotic polymer into the porous coating is achieved via the use of solvents in an aseptic process, since the coating will not withstand steam sterilization temperatures. In a work titled "Bone Cements", ISBN 3-540-67207-9, pages 16, 27-28, 141-142 and 254-258 (Springer, 2000), Dr. Klaus-Dieter Kuhn carefully distinguishes between the in-vitro polymerizing temperature of PMMA at approximately 80° C., from its in-situ temperature of approximately 46° C., from a tissue damage perspective, in particular, protein coagulation. However, Dr. Kuhn does not address the potential degradation of antibiotic effectiveness of gentamicin exposed to this temperature range. By comparison, the present inventor recognizes that inorganic compounds, both antimicrobial and osteoinductive, can withstand temperatures in excess of 400° C. and should remain therapeutically effective.

A method of treating porous coated prostheses with a biodegradable coating incorporating bioactive agents is described in the aforementioned Agrawal et al. patents. In those patents, a pharmacologically active substance, such as an antibiotic and/or an osteoinductive protein, is incorporated into a biodegradable polymer or calcium phosphate carrier and then is impregnated into the pores of the tissue-mating surfaces of the prosthesis. The biodegradable carrier dissolves over a period of weeks or months, releasing a drug to produce a pharmacological response or an osteoinductive material, e.g. bone morphogenic protein or trypsin inhibitor, which encourages bone in-growth.

Catheters having an outer coating layer which releases antimicrobial agents are described in U.S. Patent Publication No. 2008/0172011 by Heroux et al. and in U.S. Pat. No. 7,354,605 by Trogolo et al., for example. Some of these devices and other medical products utilize a water-soluble glassy material containing silver such as described in U.S. Pat. No. 5,470,585 by Gilchrist and U.S. Pat. Nos. 6,692,532 and 7,531,005 by Healy et al. Similar water-soluble antimicrobial compounds such as BACTIFREE™ and IONPURE™ water-soluble glasses are available from Mo-Sci Corporation of Rolla, Mo., and Ishizuka Glass Co., Ltd. of Nagoya, Japan, respectively.

A variety of thermoplastic polymers, due to their intrinsic biocompatibility and desirable physical properties, have found wide use as implantable biomaterials. Commonly utilized polymers include PMMA, mentioned hereinabove as 'bone cement' for fixating orthopaedic implants, and PEEK (polyether ether ketone), a colourless organic polymer thermoplastic, utilized for various procedures including interbody spinal fusion. Other implantable polymers include polyurethane and silicone, which are often employed when bending, flexing, or soft tissue interface is a prerequisite of implant utility and function. Such polymeric implants can be either molded, extruded, or thermoformed into final device configurations. Alternatively, machined polymeric implants start from block or rod forms which have been molded or extruded into initial work piece forms and are then processed into desired configurations.

Such implants commonly need to be internally fixated, whether for bone or soft tissue fixation. When such polymeric materials are interfaced with bone, often cement, screws, pins and plates are utilized to assist in polymer implant fixation. Also, such polymeric implant surfaces can be prepared with texture, grooves, undercuts or other surface features, which provides opportunity for bone ingrowth to further assist implant fixation. Osteoconductive materials, such as tricalcium phosphate, hydroxyapatite and biphasic calcium phosphate can be added to polymer resin, as filler material, in order to improve bone/implant fixation; however the ceramic particles used as filler material are generally small, approximately 10-50 microns, and poorly water soluble. Consequently any bone attachment is interfacial in nature possessing only modest shear strength.

DiFusion Technologies announced in January 2009 that it completed a series of laboratory tests of a certain silver ion-based antimicrobial technology in a PEEK spinal implant. As of the filing date of the present inventor's priority patent application, Provisional Application No. 61301698, the "CLEANFUSE MOA" mode of action section of the website "www.difusiontech.com" discloses that silver zeolite particles are compounded into the PEEK polymer during manufacture of the raw material prior to implant fabrication. Naturally occurring sodium ions in the bloodstream iontophoretically exchange with silver ions from the silver zeolite particles. The controlled cationic release of the silver ions, a broad spectrum biocide, allegedly kills hundreds of different types of microorganisms. The zeolite particles themselves, however, are not water-soluble and remain embedded within the PEEK polymer matrix without dissolving after surgical implantation.

Synthetic biodegradable polymers are often used in medicine when tissue scaffolds and/or controlled drug delivery is desired. As scaffolds, biodegradable polymers can be designed to approximate the physical and structural properties of the host tissue it replaces, while providing a suitable surface for host cell attachment and proliferation. Biodegradation of such material eliminates the need for removal of the scaffold or other device post-surgery. During the tissue remodelling process, healthy host tissue forms on the scaffold as the scaffold slowly biodegrades, ultimately leaving only native host tissue in its place. This technique can be used to regenerate new tissue such as skin, ligaments, tendons and bone. One such example is the L-C Ligament® by Soft Tissue Regeneration, Inc. in Connecticut. A braided biodegradable polymeric scaffold of poly L-lactic acid (PLLA) is implanted as an artificial cruciate ligament and is remodelled by the host's ligamentous tissue as the biopolymer biodegrades.

As drug delivery vehicles, biodegradable polymers act as a 'time release' capsule and reservoir for the bioactive agent impregnated within the polymer matrix. Drug eluting stents are a good example of the utility of such polymers in medicine.

Some of the more common synthetic biodegradable polymers include PGA (polyglycolide), PLA (polylactide), and PCA (polycaprolactone). Such polymers are synthesized by open ring polymerization and biodegrade because the polymer is hydrolytically unstable, i.e. water tends to open up and breakdown the polymer's structure. This action along with phagocytosis tends to eliminate the polymer from the patient's body. When used in drug delivery applications, biodegradable polymers are often combined in an effort to modulate the rate of hydrolysis. This in turn controls, to some extent, the elution kinetics of the bioactive agent.

Therefore the bioactive agent's elution kinetics, i.e. bioavailability, are based upon two factors: 1) the intrinsic solubility of the bioactive agent; and 2) hydrophobicity/hydrophilicity of the biodegradable polymer; for it is the hydrolytic property of the polymer that determines its: 1) biodegradation rate; and 2) the deteriorating rate of the material's mechanical, structural and physical properties.

It would be an error to assume that the erosion, that is, the removal or elimination, of the biodegradable polymer controls the elution kinetics of the bioactive agent, in other words, that the bioactive agent is still present and effective as long as the biodegradable polymer is present. This is most often not the case, since the solubility of the bioactive agent is generally far more soluble than the biodegradable polymer. Therefore, once moisture penetrates the polymer as part of the hydrolysis/biodegradation process, the same moisture solubilises, that is, dissolves, the bioactive agent, causing it to elute from the polymer. While it can be said that biodegradable polymers do in fact slow down the bioactive agent elution process, it would be fallacious to assume that the biodegradation process of the polymer was equivalent to the bioavailability of the bioactive agent within the polymer.

Biodegradable polymers therefore can retard, and to some extent control, the bioavailability of the bioactive agent. However in most clinical situations the bioactive agent elutes at a considerably faster rate that the biopolymer biodegrades. Typically, the bioactive agent is exhausted well before the polymer biodegrades.

Use of a bioactive material in a bone-implant prosthesis is described in U.S. Patent Publication No. 2003/0171820 by Wilshaw et al., for example. One preferred bioactive material is disclosed as "Bioglass® 45S5", a calcium phospho-silicate bioactive glass or glass-ceramic material, also referred to by others and herein as "45S5 Bioglass®" bioactive glass. Further examples of implants with bioactive glass are provided in U.S. Patent Publication Nos. 2008/0038534 and 2009/0208428 by Zenati et al. and Hill et al., respectively.

Mixtures including 45S5 Bioglass® material are promoted by Novobone Products, LLC of Alachua, Fla. as PerioGlas®, a synthetic absorbable, allegedly osteostimulative bone graft substitute which is mixed with sterile water, saline, blood or marrow from a patient, or with autogenous or allograft bone particles to create a paste that is applied to dental intraosseous, oral or cranio-/maxillofacial bony defects. Similarly, Nanotherapeutics, Inc., also of Alachua, Fla., provides ORIGEN DBM with bioactive glass as a malleable bone-void filler. The filler comprises human demineralised bone matrix ("DBM") and synthetic calcium phospho-silicate particles, both coated with porcine gelatin.

Other uses of 45S5 Bioglass® material include coatings for sutures with and without silver, as described by Pratten et al. in "In vitro attachment of *Staphylococcus epidermis* to surgical sutures with and without Ag-containing bioactive glass coating", J. Biomater Appl. vol. 19, pages 47-57 (2004). Glass-ceramic scaffolds formed from sintered particles of 45S5 Bioglass® which encourage bone tissue in-growth are explained by Chen et al. in "45S5 Bioglass®-derived glass-ceramic scaffolds for bone tissue engineering", Biomaterials vol. 27, pages 2414-2425 (2006).

It is therefore desirable to have improved techniques for promoting in-growth of bone or other tissue into an implant, into implant coatings, and into bone cement, preferably while also reducing the inherent risks of surgical site and implant infection.

SUMMARY OF THE INVENTION

An object of the present invention is to create biologically desirable voids in implants, implant coatings and bone cements to encourage tissue in-growth.

Another object of the present invention is to utilize water-soluble materials which resist degradation when subjected to polymerization, injection molding, extrusion and/or sterilization temperatures and which remain water soluble and biologically functional after such processing.

A further object of the present invention is to utilize water-soluble materials which resist degradation during manufacture of outer surfaces of medical implants and which enhance interstitial tissue fixation after implantation.

It is another object of the present invention to provide improved coatings on metallic implants which resist shear forces during surgical insertion and fixation of the implant.

A still further object of the present invention is to enable effective loading and antimicrobial elution kinetics for non-antibiotic antimicrobials within an implanted matrix.

This invention results from the realization that controlled delivery of one or more biologically active agents, such as ionic silver, over a desired period of time and the controlled generation of biologically desirable voids in implants, coatings, polymers or cements in proximity to damaged tissue such as bone can be provided by mixing one or more water-soluble inorganic materials into the implant, coating, polymer or cement before it is implanted in a patient.

This invention features a method for controlling the generation of biologically desirable voids in a composition placed in proximity to tissue in a patient by selecting at least one water-soluble inorganic material having a desired particle size and solubility, and mixing the water-soluble inorganic material with at least one matrix material. The matrix material is poorly water soluble in some embodiments and is biodegradable in other embodiments. In certain embodiments, the matrix material forms a substantially interconnected matrix before it is placed in a patient, either before or after the water-soluble inorganic material is mixed with it. In other embodiments, the matrix material forms a substantially interconnected matrix after it has been mixed with the water-soluble inorganic material and placed in a patient. In all embodiments, the matrix material, after mixing with the water-soluble inorganic material, is placed into the patient in proximity to tissue so that, after the matrix material has formed a substantially interconnected matrix, the water-soluble inorganic material dissolves at a predetermined rate to generate biologically desirable voids, having an average cross-sectional dimension greater than 100 microns, in the matrix material into which bone or other tissue can then grow.

In certain embodiments, the matrix material forms the interconnected matrix as a porous structure defining interstices within the porous structure, and mixing includes blending the water-soluble inorganic material within at least some of the interstices of the porous structure. The water-soluble inorganic material is then attached substantially within the interstices such that, when placed in proximity to tissue, the water-soluble inorganic material progressively dissolves to generate the biologically desirable voids by gradually exposing more of the interstices to the tissue.

In some embodiments, the matrix material includes a human allograft with cancellous bone which forms the porous structure, and the water-soluble inorganic material is attached using a binder such as a biocompatible adhesive. In other embodiments, the water-soluble inorganic material is attached by heating the blended material to fix the water-soluble inorganic material within the interstices.

In some embodiments, at least a majority of the water-soluble inorganic material is particles having dimensions averaging below 100 microns, preferably between about 10 microns to about 50 microns. In one embodiment, the average dimension of the water-soluble inorganic material is at least five times smaller than the average dimension of the interstices. In certain embodiments, the interstices have average dimensions ranging from greater than 100 microns to about 1000 microns, preferably between 200 microns to 800 microns.

Preferably, the water-soluble inorganic material includes at least one constituent having osteoinductive properties, at least one non-antibiotic constituent having antimicrobial properties, or both types of constituents. In some embodiments, the water-soluble inorganic material is a water-soluble glass, preferably a bioactive glass such as 45S5 Bioglass® bioactive glass and/or BACTIFREE antimicrobial glass. Further, the water-soluble inorganic material can be selected to have at least two different particle sizes and/or at least two different formulations which have different solubilities and/or different osteoinductive concentrations and/or different non-antibiotic antimicrobial agents and/or concentrations of one or more types of non-antibiotic antimicrobial agents.

In some embodiments, particles having dimensions averaging between greater than 100 microns to about 1000 microns are selected as at least one water-soluble inorganic material. In other embodiments, at least some particles of the water-soluble inorganic material have a particle length that is at least twice as great as the width of the particle. Preferably, the particle length averages between about 400 microns to about 1,200 microns and the particle width averages between about 150 microns to about 800 microns.

In several preferred embodiments, the water-soluble inorganic material includes an effective amount of at least one non-antibiotic antimicrobial agent. In one embodiment, the antimicrobial agent includes a heavy metal such as silver that is releasable in ionic form. In another embodiment, some of the water-soluble inorganic material includes a first concentration of an antimicrobial agent while other water-soluble inorganic material includes a second concentration of the antimicrobial agent that is different from the first concentration.

Poorly-water-soluble matrix material includes a bone cement such as polymethylmethacrylate in some embodiments, and in some other embodiments includes an organic polymer thermoplastic material such as polyether ether ketone. In other embodiments, the matrix material has at least one substance which alters its hydrophilicity to change the rate of water absorption, which in turn affects the solubility and therefore the rate of dissolution of the water-soluble inorganic material.

In yet other embodiments, the matrix material is poorly-water-soluble porous or roughened implant coating material made of crystalline particles, such as a ceramic or a mineral such as hydroxyapatite, tricalcium phosphate or biphasic calcium phosphate, or metallic particles such as titanium or stainless steel. In one embodiment, the water-soluble inorganic materials are blended with the matrix particles and then heated to secure the water-soluble inorganic material to the matrix particles, such as by sintering or other heat fusion technique. In some embodiments, mixing includes blending the water-soluble inorganic material with matrix particles and heating the blended material to secure the matrix particles to each other and to at least a portion of an outer surface of a metallic implant to form the interconnected matrix as a coating defining the biologically desirable voids at least partially occupied by the water-soluble inorganic material such that, when placed in proximity to tissue, the water-soluble inorganic material dissolves to progressively enlarge the biologically desirable voids.

In one embodiment, the metallic implant is a bone fixation device such as an external fixator pin or a bone screw having a shaft and having threads on a threaded region for engaging bone, and the blended material is placed about at least the threaded region. Preferably, water-soluble material containing at least one non-antibiotic antimicrobial agent is placed about at least a portion of the shaft of the fixation device. In another embodiment, the metallic implant is a component of an artificial joint such as hip implant.

The invention may be expressed as a method for controlling the generation of biologically desirable voids in a composition placed in proximity to tissue in a patient by selecting at least one water-soluble inorganic material having a desired particle size and solubility, and selecting a poorly-water-soluble matrix material having an interconnected matrix as a porous structure disposed on at least a portion of the outer surface of an implant and defining interstices within the porous structure. The method further includes blending the water-soluble inorganic material within at least some of the interstices of the porous structure. The water-soluble inorganic material is then attached within the interstices such that, when placed in proximity to tissue, the water-soluble inorganic material progressively dissolves to generate the biologically desirable voids by gradually exposing more of the interstices into which the tissue can grow to assist fixation of the implant within the patient.

The invention may be further expressed as a method for controlling generation of biologically desirable voids in a thermoplastic material placed in proximity to tissue by selecting at least one water-soluble inorganic material having a desired particle size, and mixing the water-soluble inorganic material with at least one thermoplastic material. The mixture is solidified, and the solidified mixture is placed into a patient in proximity to tissue so that the water-soluble inorganic material dissolves at a predetermined rate to generate biologically desirable voids in the thermoplastic material into which tissue can then grow. In some embodiments, the thermoplastic material undergoes injection, transfer or compression molding, or extrusion after it is mixed with the water-soluble material and before it is solidified. In other embodiments, solidifying the mixture includes processing the solidified mixture to a desired configuration, and placing the solidified mixture includes placing the desired configuration into the patient.

The invention may also be expressed as a method for controlling generation of biologically desirable voids in a bone cement placed in proximity to bone by selecting at least one water-soluble inorganic material having a desired particle size, and mixing the water-soluble inorganic material with at least one bone cement material. The mixture is placed into a patient in proximity to bone so that the water-soluble inorganic material dissolves at a predetermined rate to generate biologically desirable voids in the bone cement into which bone can then grow.

The invention may yet further be expressed as a method for controlling generation of biologically desirable voids, such as interstices between braided fibers, in a biodegradable composition placed in proximity to tissue by selecting at least one water-soluble inorganic material having a desired particle size, and blending the water-soluble inorganic material with at least one biodegradable matrix material. The water-soluble inorganic material is attached by at least one of utilizing a biocompatible binder or heating the blended material to fix the water-soluble inorganic material to the biodegradable matrix material. The mixture is placed into a patient in proximity to tissue so that the water-soluble inorganic material dissolves at a predetermined rate to generate biologically desirable voids in the biodegradable matrix material into which bone can then grow.

BRIEF DESCRIPTION OF THE DRAWINGS

Preferred embodiments of the invention are explained in more detail with reference to the drawings, in which:

FIG. 5A is a partial cross-sectional view of a hip implant placed in a femur bone and having a porous metal coating loaded with dissolvable particles according to the present invention;

FIG. 5B is an enlarged view of a portion of FIG. 5A showing water-soluble inorganic particles occupying interstices of the porous metal coating upon initial implantation;

FIG. 5C is a subsequent view showing partial dissolution of the water-soluble inorganic particles;

FIG. 5D is a yet later view showing further particle dissolution and bone growth into the interstices of the porous metal coating to assist fixation of the implant;

FIG. 6A is a schematic perspective view of a PEEK implant solidified after mixing with water-soluble inorganic particles according to the present invention;

FIG. 6B is a schematic enlargement of a portion of the PEEK implant showing the soluble particles on the surface of the implant;

FIG. 6C is a similar view showing biologically desirable voids generated in the PEEK implant after the water-soluble inorganic particles have dissolved; and FIG. 7 is a schematic view of a portion of a cancellous bone allograft partially loaded with water-soluble inorganic particles according to the present invention.

DETAILED DESCRIPTION OF THE PRESENTLY PREFERRED EMBODIMENTS

Figure 1:
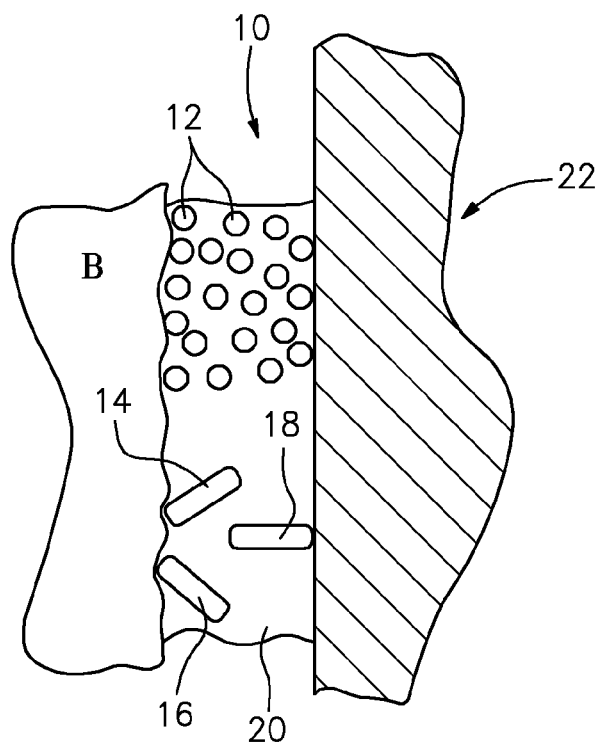
FIG. 1 is an elevational cross-sectional view of water-soluble particles in bone cement placed between bone and an implant according to one embodiment of the present invention.

This invention may be accomplished by selecting one or more water-soluble inorganic materials having a desired particle size and solubility, and mixing the water-soluble inorganic materials with at least one poorly-water-soluble matrix material in some constructions, and with at least one biodegradable matrix material in other constructions. The mixture is placed into a patient in proximity to bone or other tissue so that, after the matrix material has formed a substantially interconnected matrix, the water-soluble inorganic material dissolves at a predetermined rate to generate biologically desirable voids in the matrix material into which bone or other tissue can then grow to fixate the matrix material within the patient.

The term "mixture" as used herein broadly refers to any combination of water-soluble inorganic material with matrix material or any placement of water-soluble inorganic material within matrix material. The term "substantially interconnected matrix" as used herein broadly refers to physical continuity of matrix material ranging from open-cell lattices and scaffolds to solid monoliths of matrix material. In certain constructions, matrix material forms a substantially interconnected matrix before it is placed in a patient, either before or after the water-soluble inorganic material is mixed with it. Porous sintered metal and/or hydroxyapatite particle coatings and certain allografts are an example of a pre-formed interconnected matrix into which water-soluble inorganic particles are then placed, and thermoplastic and bioabsorbable materials are examples of matrix materials which solidify into interconnected matrices after water-soluble inorganic particles are mixed therein. In other constructions, a matrix material such as bone cement forms a substantially interconnected matrix after it has been mixed with the water-soluble inorganic material and placed in a patient.

In several of the constructions described in more detail below, the matrix material forms the interconnected matrix as a porous structure defining interstices within the porous structure, and mixing includes blending the water-soluble inorganic material within the interstices of the porous structure. The water-soluble inorganic material is then attached within the interstices such that, when placed in proximity to tissue, the water-soluble inorganic material progressively dissolves to generate the biologically desirable voids by gradually exposing more of the interstices to the tissue. In other words, the biologically-accessible voids increase in size and become biologically desirable as the interstices are restored, revealed, enlarged or re-created by progressive dissolution of the water-soluble inorganic material. The increasing volume of the voids approaches and would eventually match the original volume of empty space of the interstices that existed before the water-soluble inorganic material was blended into a selected percentage of the interstices, except to the extent that tissue grows into the voids to occupy that gradually exposed space.

Preferably, the water-soluble inorganic material contains at least one inorganic constituent that has at least one of the following properties: osteoconductive, osteoinductive and/or antimicrobial. The term "osteoconductive" as used herein is intended to include materials that provide favourable conditions or surface properties to allow osteoblast growth and bone material deposition on or into such materials. The term "osteoinductive" as used herein is intended to include certain materials, such as bioactive materials, osteogenic materials, and osteostimulative materials, which induce osteoblast infiltration, growth and bone matrix deposition via stimuli, signalling and/or growth factors or which otherwise accelerate natural healing processes and/or the quality of bone regeneration. The term "non-antibiotic antimicrobial" as used herein refers to substances which inhibit the growth and reproduction of microorganisms, but excludes antibiotic substances. The term "antibiotic" as used herein refers to an organic substance produced by a microorganism, and/or a semisynthetic equivalent organic substance, that either inhibits or kills other microorganisms.

Suitable water-soluble inorganic materials include antimicrobial water-soluble glasses which, in some constructions, contain silver as a non-antibiotic antimicrobial agent as disclosed in U.S. Pat. Nos. 5,049,139 and 5,470,585 by Gilchrist and Nos. 6,692,532 and 7,531,005 by Healy et al., which are incorporated herein by reference in their entirety. Similar water-soluble silver-containing compounds such as BACTI-FREE and IONPURE water-soluble glasses are available from Mo-Sci Corporation of Rolla, Mo., and Ishizuka Glass Co., Ltd. of Nagoya, Japan, respectively. Suitable osteoinductive water-soluble inorganic materials include those disclosed in U.S. Patent Publication No. 2003/0171820 by Wilshaw et al. and No. 2009/0208428 by Hill et al., which are also incorporated herein by reference. One preferred material disclosed by both Wilshaw et al. and Hill et al. is "Bioglass® 45S5", a calcium phospho-silicate bioactive glass or glass-ceramic, also referred to as "45S5 Bioglass®" bioactive glass hereinafter.

A bone cement 10 containing a number of generally spherical water-soluble inorganic particles 12 and elongated water-soluble inorganic elements 14, 16 and 18 within a poorly-soluble cement matrix 20 in one construction according to the present invention is illustrated in FIG. 1 securing implant 22 to bone B of a patient. Poorly soluble cement matrix 20 is a conventional cement in this construction such as PMMA (polymethylmethacrylate) into which several types of water-soluble materials have been added by mixing prior to placement in the patient; cement with entrained water-soluble materials then is placed as a putty between bone B and implant 22. Insertion of the implant into a reamed bone canal causes the setting PMMA putty to migrate into the porosities of the cancellous portion of bone B as well as into flutes, undercuts, or other surface features of the implant 22. Hardening of the interdigitated PMMA matrix 20 interlocks the implant 22 with the bone B to fixate the implant 22 within the patient. An upper limit to the amount of water-soluble inorganic materials that can be mixed into the matrix 20, especially when utilized for weight-bearing bone repairs, is reached when the physical properties of the PMMA matrix would degrade below certain performance standards set by such organizations as the International Standards Organization, including ISO Standard No. 5833.

Water-soluble inorganic particles 12 preferably are generally spherical in this construction and have an average particle diameter of greater than 100 microns to about 1000 microns, preferably between about 150 microns to about 800 microns, and more preferably between about 200 to about 600 microns. Particles 12 are drawn as open circles in FIG. 1 for simplicity of illustration. The term "generally spherical" as utilized herein refers to a particle whose length is less than twice its width and includes polyhedrons and other non-uniform shapes, such as those obtained by milling blocks, ingots or other larger formations of water-soluble inorganic material. Particles can be sorted and sized using conventional techniques including sieving. In some constructions, particles 12 are selected to have at least two different particle sizes and/or at least two different formulations which have different dissolution rates and/or different concentrations of one or more osteoinductive and/or antimicrobial constituents such as found in bioactive glasses. The parameters of size (including shape and dimensions) and formulation, as well as hydrophilicity of the matrix material in some embodiments, are adjusted to alter the dissolution rate of the water-soluble particles 12.

In the FIG. 1 construction, the size of the water-soluble inorganic particles directly determines the size of the biologically desirable voids that are generated as the particles dissolve. In other constructions where porosity of the matrix material is intrinsically enhanced, such as in Kryptonite™ bone cement available from Doctors Research Group, Inc. of Southbury, Conn., for repairing non-weight-bearing cranial defects, smaller water-soluble inorganic particles can be utilized according to the present invention. Upon setting, Kryptonite™ bone cement itself creates a porous closed-cell matrix for bone ingrowth and implant integration. In other words, the Kryptonite™ bone cement material enhances its own porosity after placement in the patient. Mixing water-soluble inorganic particles according to the present invention before or during delivery of the Kryptonite™ bone cement into a cranial defect enables tailoring of the size and number of biologically desirable voids that are generated, as well as adding antimicrobial and/or osteoinductive bioactive agents as desired. If a surgeon chooses to not substantially increase the size or number of biologically desirable voids that are ultimately created, much smaller water-soluble inorganic particles below 100 microns, preferably 10 microns to 50 microns in average dimension, can be utilized.

Figure 4:
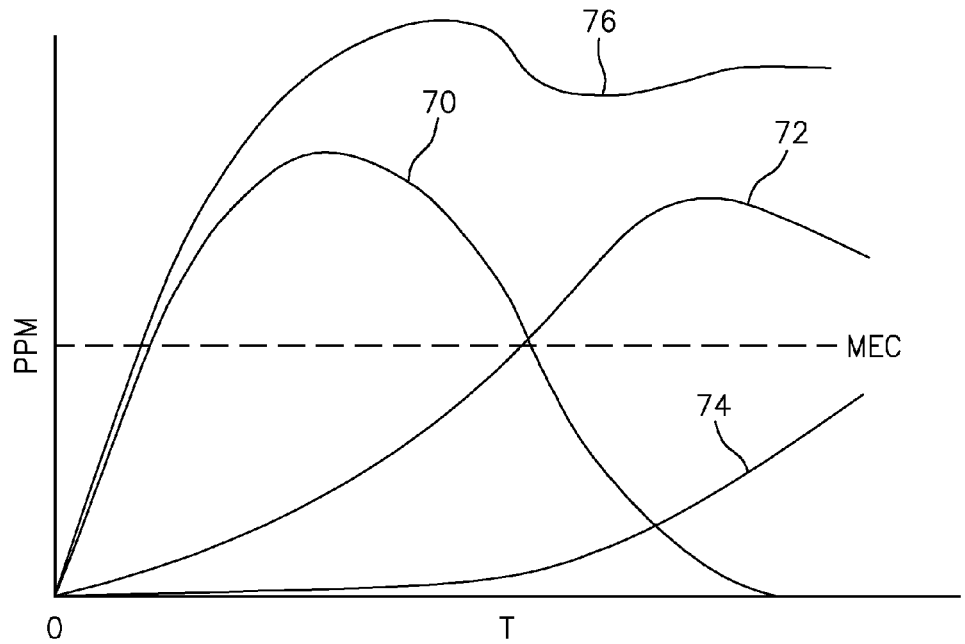
FIG. 4 is an ionic silver elution graph showing the amount of silver ions releasable over time for some of the embodiments of FIGS. 1 and 2.

Preferably, the particles 12, FIG. 1, also contain one or more non-antibiotic antimicrobial agents such as metals which release active ions such as silver ions, copper ions, zinc ions and/or other biocidal cationic ions. Intrinsic properties to be considered for suitable biocidal agents include patient safety, cytotoxicity, effective dose, duration of bioavailability, and spectrum of microorganisms affected. Concentration and/or combinations of such non-antibiotic antimicrobial agents can be adjusted to alter antimicrobial ionic release profiles. Concentration of one or more non-antibiotic antimicrobial agents as well as the formulation of the water-soluble inorganic compound are several variables that can be adjusted to alter ionic release kinetics as discussed below in relation to FIG. 4 illustrating overall silver ion release over time.

Water-soluble inorganic elements 14, 16 and 18 have a length that is at least twice as great as the width of those elongated particles to form elongated "pockets" for bone in-growth upon dissolution. Preferably, the length averages between about 400 microns to about 1,200 microns, more preferably about 1000 microns, and the width averages between about 150 microns to about 800 microns, more preferably between about 250 microns to about 550 microns, for those elongated cylindrical or lozenge-shaped particles. It is desirable for the edges of elements 14, 16 and 18 to be rounded to reduce stress risers in the bone cement matrix 20, especially after the elements dissolve. Techniques for rounding the edges include cutting the elements from a longer rod of water-soluble material using flame or laser, or heating the elements formed by cutting or molding to soften and smooth the edges post-forming. Other processes of manufacturing elongated particles include extruding or spinning fibers of selected water-soluble material and then cutting the fibers to desired lengths, or molding or casting such particles directly to form such shapes. Additionally, the parameters of size (including length and/or width) and formulation are adjusted as desired to alter the dissolution rate of the water-soluble elements 14, 16 and 18.

The solubility, and therefore the dissolution rate, of the water-soluble inorganic particles within a polymeric matrix such as bone cement can also be adjusted by altering the hydrophilicity of the matrix material 20, such by adding one or more of the following substances, in order of increasing hydrophobicity: methyl acrylate; ethyl acrylate; butyl methacrylate; and styrene. Other, non-bone-cement, implantable polymers which are even more hydrophilic include polyurethanes, polyvinylpyrrolidone, and hydroxyethyl methacrylate. Any medical-grade substance having a different rate of water absorption when mixed into the matrix according to the present invention will affect the rate of dissolution of the water-soluble inorganic particles.

Figure 2:
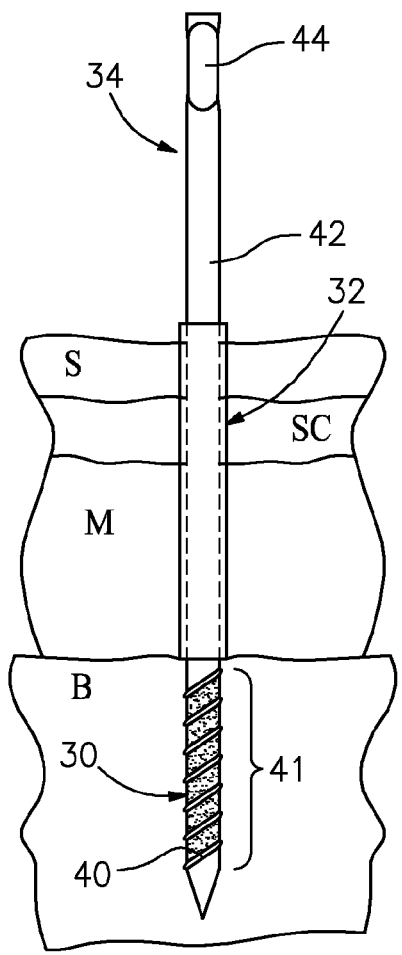
FIG. 2 is an elevational cross-sectional view of water-soluble material coatings on two regions of a fixation device implanted in a patient according to another embodiment of the present invention.

High-temperature-resistant, high-shear-strength-resistant coatings 30 and 32 according to another aspect of the present invention are shown in FIG. 2 on external fixator pin 34, which is depicted with threads 40 in threaded region 41 engaged in bone B and with shaft 42 extending distally through muscle M, subcutaneous tissue SC, and skin S comprising the dermis and epidermis. A drive surface 44 is formed on the distal end of pin 34 to engage a drive mechanism to set the threaded region 41 into bone B.

Coating 30 is formed on threaded region 41, preferably formed as illustrated in stippling on the root portions of threads 40, which serve as the initial engagement and cutting portion of the fixator 34. Several different coating techniques are described below in relation to FIGS. 3A and 3B which can be utilized to form coating 30, FIG. 2. Over time, as the water-soluble inorganic material dissolves, autologous bone tissue engages the porous coating 30, enabling bone in-growth into the voids to enhance fixation of the fixator 34.

Preferably, coating 32 is formed on shaft 42 containing one or more non-antibiotic antimicrobial agents to resist percutaneous migration of microbes along shaft 42 of the fixator 34. In some embodiments, coating 32 is formed of the same or similar inorganic material as coating 30 and in other embodiments different inorganic materials are utilized according to the present invention. Preferably, water-soluble glass particles are fused to shaft 42 via heat, causing the particles to solidify as a smooth glassy coating 32.

Several different techniques can be utilized to form porous inorganic coatings according to the present invention. In one technique, a porous matrix of poorly-soluble material, such as metallic or crystalline particles, is formed on a substrate, such as a metallic implant, by conventional processes. The formed porous matrix typically has pores ranging from 100 microns to 1000 microns, preferably between 200 microns to 800 microns, and then water-soluble inorganic particles are added by blending into the porous matrix a slurry formed with a liquid, preferably non-aqueous carrier or are blown or aspirated into the pores. This "mixture" is then heated to the sintering temperature of the inorganic compound which evaporates the liquid carrier and fuses the water-soluble inorganic particles in place within the matrix. The water-soluble inorganic particles have average sizes ranging from about 2 microns to about 50 microns, preferably about 5 microns to about 10 microns, so they can infiltrate the existing pores or interstices of the matrix material. In one construction, the average dimension of the water-soluble inorganic material is at least five times smaller than the average dimension of the interstices.

Figure 3A:
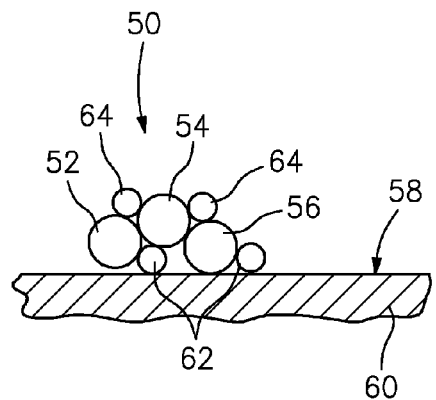
FIG. 3A is an elevational cross-sectional view of water-soluble particles and poorly-water-soluble metallic or crystalline particles on an implant prior to heating.
Figure 3B:
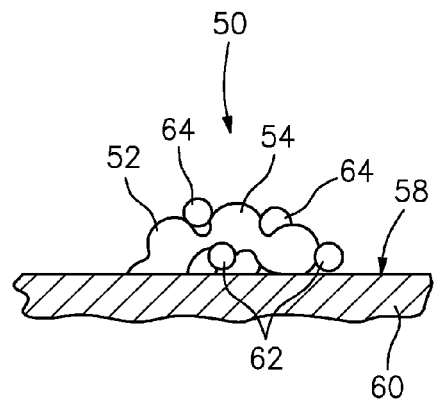
FIG. 3B is an elevational cross-sectional view of the water-soluble particles and metallic or crystalline particles on the implant of FIG. 3A after heating.

Another manufacturing technique is illustrated in FIGS. 3A and 3B to form coating 50 of metallic particles or crystalline 52, 54 and 56 on outer surface 58 of metallic implant 60 intermixed with first water-soluble inorganic particles 62 and second water-soluble particles 64. The combined metal-inorganic compound matrix mixture is then heat sintered to join the matrix together as depicted in FIG. 3B. In another embodiment, water-soluble particles 62 and 64 are applied simultaneously with all metallic or crystalline particles 52, 54, 56 similar to the teachings of Roberts in U.S. Pat. Nos. 4,813,965 and 4,938,409, which are incorporated herein by reference for thermal spraying and other particle bonding techniques onto various types of metallic implants. When one technique of thermal spraying is utilized, the water-soluble particles and the poorly-water-soluble particles are delivered as a single mixture onto the implant through the same nozzle or orifice and, in other techniques, are delivered using separate nozzles, orifices, or delivery mechanisms to build a mixed coating on the implant. Preferably for all constructions according to the present invention, substantially each of the poorly-water-soluble particles become connected with at least one other poorly-water-soluble particle so that a substantially interconnected matrix of the poorly-water-soluble particles is formed.

Average matrix particle sizes for the metallic particles, such as titanium particles, or for crystalline particles, such as hydroxyapatite, range in some constructions from about 100 microns to about 800 microns. Preferred average particle sizes for the water-soluble inorganic particles are about the same size to less than half the size of the metallic or hydroxyapatite particles, more preferably ranging from about 100 microns to about 400 microns, even more preferably about 200 microns to about 300 microns.

Heating the implant 60 with coating 50 causes the outer surfaces of metallic particles 52, 54, 56 to flow and form "necks" which bond the particles 52, 54, 56 to each other, to surface 58, and to first and second water-soluble particles 62 and 64 as shown in FIG. 3B. Porosity commences or increases after implantation of coated implant 60 in a patient as particles 62 and 64 begin to dissolve.

In yet other coating techniques, a metallic surface is roughened or textured. Metallic particles are then applied first followed by water-soluble inorganic particles or, alternatively, together with water-soluble inorganic particles, to form coatings which generate voids upon inorganic particle dissolution according to the present invention. Metallic or mineral particles can also be applied by plasma spray or other conventional technique, especially techniques utilizing heat to fuse the matrix particles to a metallic implant. In one construction, an implant having a porous coating is dipped into molten water-soluble glass to mix water-soluble inorganic particles into the porous coating. The thermal coefficient of expansion of the implant materials relative to the water-soluble glass should be considered.

In certain constructions, water-soluble inorganic materials are blended, such as by infusion, into interstices, that is, existing pores, of porous coated implants and then sintered, fused or otherwise attached to fix the water-soluble inorganic material in place. Suitable porous matrix coatings can be made from a variety of materials, including one or more of the following: ceramics; crystalline minerals such as hydroxyapatite, tricalcium phosphate or biphasic calcium phosphate; and metallic beads or particles made from materials such as titanium, tantalum or stainless steel. In other constructions, such matrix materials are first applied as a coating which may not have interstices, but does have pits, craters or other surface irregularities to serve as biologically desirable voids, and then the water-soluble inorganic particles are added.

Alternatively, the implant surface can be intentionally roughened by bead blasting or other comparable surface treatment, to create pits, craters or other surface irregularities as voids into which bone can later attach and perhaps infiltrate. Water-soluble inorganic particles are then fused or otherwise fixed to the surface of such roughened implant surfaces to provide antimicrobial and/or osteoinductive properties during dissolution. The ratio of the average width or depth of the surface irregularities to the average cross-sectional dimension of the water-soluble particles fixed thereto is typically greater than 1:1, preferably greater than 5:1, more preferably at least 10:1, and in some constructions ranges from about 30:1 to about 100:1. For example, surface irregularities having an average width of 400 microns would have a ratio of 40:1 relative to water-soluble particles having an average diameter of 10 microns, while surface irregularities having an average width of 600 microns would have a ratio of 60:1 relative to the same water-soluble particles.

One of the major advantages of water-soluble inorganic compounds is the ability to tailor dissolution rates via composition formulation and osteoinductive and/or non-antibiotic antimicrobial concentration within the inorganic compound formulation to control both the rate and size of void generation as well as release rates of antimicrobial and/or osteoinductive agents according to the present invention. Tailored as desired, inorganic compound particle size and selection of one or more matrix materials, including characteristics such as hydrophobicity/hydrophilicity, further enhance design flexibility regarding bioactive elution kinetics. Inorganic compound dissolution rates, also referred to as compound solubility, can span several orders of magnitude, providing greater sensitivity and range than alternative technologies.

As described in the Background above, Kuhn et al. utilize antibiotic compounds that dissolve quickly in the presence of moisture, eluting the antibiotic within days, if not hours. Biodegradable organic polymers with bioactive agents, as taught by Agrawal et al, biodegrade very slowly over a period of months, perhaps longer. However, since the biodegradation of the polymer is largely achieved via hydrolysis, bioactive agents within the polymer elute at a significantly faster rate than the polymer's biodegradation process. Consequently, the bioactive agent's effective bioavailability is gone long before the polymer itself fully biodegrades. Few technologies can span the clinical need of providing osteoinductive and/or antimicrobial elution kinetics over a span of days-to-years; water-soluble inorganic compounds utilized according to the present invention meet this requirement. By combining inorganic compounds of different solubilities, osteoinductive and/or antimicrobial concentrations, particle sizes and/or matrix materials according to the present invention, one can generate osteoinductive and/or antimicrobial elution kinetics to meet specific clinical needs as desired.

From an orthopaedic implant perspective, there is an immediate need for post-operative surgical site infection prevention as well as a longer-term need for prophylactic infection protection for months following implantation. An antimicrobial elution profile of three different water-soluble inorganic silver compounds, having different intrinsic solubilities and silver concentrations, is illustrated in FIG. 4. Ionic silver elution profiles 70, 72 and 74 are represented in PPM (parts per million) over time T relative to a target minimum effective biocidal concentration MEC, shown with dashed line, required to have a biocidal effect on a targeted microorganism, in other words, more than a biostatic effect. Elution profile 70 represents a water-soluble inorganic silver compound which is formulated to dissolve quickly, over a periods of days, at a higher enough ionic silver concentration to exceed the minimum effective concentration MEC required to have a biocidal effect on one or more targeted pathogenic microorganisms.

Elution profile 72 represents a second water-soluble inorganic silver compound that releases its biocidal ionic silver over a period of weeks-to-months, due to either the compound's formulation as it affects intrinsic solubility, silver concentration, and/or particle size. In this example, elution profile 72 bridges the gap between immediate post-op infection prevention and longer term, latent infection protection. Elution profile 74 represents a much slower dissolving inorganic compound, requiring higher silver concentrations, due to its slow dissolution rate in order to exceed pathogen MEC requirements to protect the patient over the longer term from latent infections. Throughout the period elution kinetics are additive, therefore a composite bioactive elution profile is represented by elution profile 76, essentially spanning the entire period, from days-to-months, with a biocidal concentration of ionic silver in excess of the MEC required for the targeted pathogens.

Returning to types of implants utilizing porous coatings loaded with water-soluble inorganic particles according to the present invention, there are a number of such implants serving as components of artificial joints such as those connecting a femur to an acetabulum of a hip bone. A portion of a hip implant 80, FIG. 5A, is illustrated cross-section with a portion of its outer surface carrying a porous metal coating 90. Implant 80 is shown placed in a medullary canal of femur bone B. Porous metal coating 90 is loaded with water-soluble inorganic particles 94 occupying the volume of interstices 96 defined by sintered metallic particles 92 of the porous metal coating 90, which are schematically illustrated in enlarged view in FIGS. 5B-5D with bone B having cancellous portion CN. Implant 80 is shown upon initial implantation in FIG. 5B substantially fully loaded with water-soluble inorganic particles 94, shown as open circles for simplicity of illustration. In one construction, the interstices are more than ninety percent filled. In other, partially-filled constructions, the interstices are ten percent to ninety percent filled, preferably at least thirty percent to sixty percent filled. In yet other constructions, especially for certain flexible or compressible allografts as described in more detail below, a lesser filling of five percent to fifty percent, more preferably ten percent to thirty percent, is utilized to achieve the present invention while maintaining the physical properties of the allografts.

A subsequent view of implant 80 after passage of a number of weeks is illustrated in FIG. 5C showing partial dissolution of the water-soluble inorganic particles 94. This represents at least one of a reduction in size or quantity of particles 94 which have been exposed to bodily fluids and, in some constructions, disappearance of particles formulated to have a faster dissolution rate. A yet later view is illustrated in FIG. 5D showing further particle dissolution and bone growth IN of cancellous portion CN into the interstices 96 of metallic particles 92 of the porous metal coating 90 to assist fixation of the implant.

Another aspect of the present invention employs relatively large inorganic water-soluble particles, preferably having average dimensions greater than 100 microns to about 800 microns, which are added as filler material to a polymer for injection molding, extrusion, or any other form of thermoplastic processing, fabrication or production in such a manner so that, when the finished device is implanted, the water-soluble inorganic particles dissolve at a predetermined rate to generate a textured or porous implant surface structure into which new bone can grow. This provides for better interdigitation of bone ingrowth within the biologically desirable voids of the porous surface structure of the implant, enhancing implant fixation and improving the shear strength of the bone/implant interface.

In one construction, interbody cages for spine fusion are manufactured by directly compounding water-soluble inorganic particles into a poorly-soluble organic polymer thermoplastic matrix materials such as polyether ether ketone (PEEK). A cervical cage 100 according to the present invention is shown in FIG. 6A. The surface within dashed circle 6B,6C is illustrated schematically in enlarged view in FIG. 6B having a PEEK matrix 102 with water-soluble inorganic particles 104, such as water-soluble glass particles 106 and 108, mixed therein. In one construction where water-soluble inorganic particles 104 are mixed throughout matrix 102, a cross-sectional view through implant 100 would be similar to that of the bone cement shown in FIG. 1 above. After implantation, the particles 104 dissolve to generate biologically desirable voids 110, FIG. 6C, such as voids 112 and 114 generated by particles 106 and 108, FIG. 6B, respectively.

Additionally if the water-soluble inorganic compound particles are made of materials such as Hench's 45S5 'Bioglass' compound, or the like, upon dissolution osteostimulative signalling molecules will be released into the immediate bone/polymer implant interface milieu such that osteoinductive signalling will enhance osteoblast recruitment and bone matrix deposition at the implant's porous/textured surface. This bone matrix deposition stimulation accelerates and enhances bone ingrowth and polymer implant fixation.

Likewise, should the water-soluble inorganic compound particles include silver oxides or other heavy oxides metals, upon dissolution ionic silver is released, providing broad spectrum antimicrobial prophylaxis to the implant's surface, while simultaneous creating a porous/textured implant surface for osteoblast infiltration, bone matrix deposition and ultimately enhanced implant fixation.

One or more osteoinductive inorganic compound particles of various sizes can be mixed, i.e. combined with one or more antimicrobial inorganic compound particles of various sizes, to create an admixture of particles that provide the implant with both osteoinductive and antimicrobial properties, while creating a porous/textured implant surface structure to stimulate osteoblast infiltration and bone matrix deposition. Furthermore, by mixing various inorganic water-soluble particles together, having different intrinsic solubility, one can affect the dissolution rate of said particles, effectively controlling the elution kinetics, i.e. bioavailability, of the bioactive agent and consequently improve/enhance the clinical benefit/utility of the invention.

A similar biological effect can also be achieved by adding silver oxide or other heavy metal oxides to an osteoinductive Bioglass-like inorganic compound formulation. Upon dissolution, a single inorganic water-soluble compound can produce both osteostimulative signalling and antimicrobial prophylaxis. Likewise, by combining particles of more than one silver oxide containing Bioglass-like inorganic compounds, having different intrinsic solubility, one can tailor the elution kinetic profile, i.e. the bioavailability, of the dissolution ions such that clinical benefit/utility can be optimized.

Another aspect of the present invention utilizes water-soluble inorganic particles within biodegradable polymers such as PGA (polyglycolide), PLA (polylactide), and PCA (polycaprolactone). Such polymers are synthesized by open ring polymerization and biodegrade because the polymer is hydrolytically unstable, i.e. water tends to open up and breakdown the polymer's structure. This action along with phagocytosis tends to eliminate the polymer from the patient's body.

The present invention includes employing water-soluble inorganic compounds for antimicrobial and tissue regeneration applications such as biodegradable polymer scaffolds. These scaffolds are physical structures meant to substitute for host tissue until such time that host tissue remodels the structure as the structure biodegrades. Such implantable devices still have need for antimicrobial prophylaxis and in many cases the need to stimulate tissue ingrowth as part of remodelling and/or fixation process. Water-soluble inorganic compounds provide the intrinsic flexibility, via composition formulation, to control solubility of the particle, therefore the elution kinetics, i.e. bioavailability, of the bioactive agent. Therefore, as long as moisture in allowed into the biodegradable polymer, which is how the polymer biodegrades, the dissolution of the particle is predicated more upon the solubility of the water-soluble inorganic compound than the hydrolytic property of the polymer. This means one can intentionally design a particle's dissolution and, therefore, bioactive agent bioavailability, to be: (1) faster than the polymer's biodegradation; i.e. like most conventional bioactive agents such as antibiotics and growth factors; (2) comparable to the polymer's biodegradation, such that the bioactive will be present as long as the biodegradable polymer is present; or (3) slower than the polymer's biodegradation, i.e. allowing the water-soluble inorganic particle to remain bioavailable, long after the biodegradable polymer erodes.

The latter two bioavailability options are exceedingly difficult to attain by conventional techniques, since most bioactive agents are significantly more soluble than the biodegradable polymer in which it is encapsulated. All three options are readily achievable using methods of the present invention.

As one example, the L-C Ligament® device mentioned above in the Background, can be modified according to the present invention to carry both osteoinductive, i.e. Bioglass®-like, and antimicrobial, i.e. silver oxide based, water-soluble inorganic particles to provide novel patient benefit/clinical utility by: (1) enhancing or accelerating bone ingrowth into the bony scaffold attachment region, such as the tibia and femur, of the biodegradable implant; as well as (2) providing antimicrobial prophylaxis to the implant post-surgery and throughout the entire implant biodegradation process, or even post-biodegradation.

Another advantage of water-soluble inorganic compounds, applicable to this topic is the material's high glass transition temperature and variety of physical forms, making such material conducive to a wide variety of thermoplastic applications/processes. The material's high glass transition temperature allows particles to be injection molded, extruded, coated or any other form of thermoplastic and/or thermosetting polymer processing, without the fear of degradation of the bioactive agent. Many antibiotics, growth factors and other organic bioactive agents cannot withstand the processing temperature associated with many form of commercial plastic processing. This is not a concern with water-soluble inorganic compounds with melt temperatures in the 1,000° C. range and glass transition temperatures typically ranging from 500° C.-800° C. Furthermore such glassy materials can be extruded and/or spun into glassy fiber, like fiberglass, and needle punched, woven, knit, braided, etc. into various fabrics and materials.

Returning to the L-C Ligament® example again, it is a braided biodegradable polymer scaffold having interstices among braided fibers. Braided fibers are one example of "interlocked fibers", which term is used herein to also include other types of woven, twisted, non-woven felt-type, or other combination of fibers that form gaps or other spaces between the fibers. In one construction according to the present invention, water-soluble inorganic particles are extruded directly into the poly L-lactic acid (PLLA) fibers, which are then braided into the ligament scaffold. Alternatively, one could choose to extrude or spin glassy water-soluble inorganic fibers and blend the fibers with the PLLA fibers, and then braid the composite fibers into the desired ligament scaffold. Or lastly, one can impregnate, through various conventional techniques, water-soluble inorganic particles within the interstices of a fabricated PLLA scaffold, similar to the process described hereinabove for a porous metal coated implant, fixing such particles in place with heat or one or more biocompatible/biodegradable polymers or adhesives, such as polyethylene glycol (PEG), polyinylpyrrolidone (PVP), polyvinyl alcohol (PVA), hyaluronan, and alginate or other forms of polysaccharides.

Another aspect of the present invention utilizes allografts, preferably human allografts. An allotransplantation is the transplantation of cells, tissues or organs sourced from a genetically non-identical member of the same species as the recipient. The transplant is called an allograft, which is intended herein to include the term homograft. A variety of transplantable tissues can be used as allografts, including ligaments, tendons and bone. Such tissues either have the need to attach to bone, or are bone. It can be appreciated therefore that water-soluble inorganic compounds that are osseostimulative can play an important role in the attachment of ligaments and tendons to bone, or if bone, can aide in the regeneration of new bone. Also, such tissue and surgical transplantation have a need for antimicrobial prophylaxis to reduce of risk of surgical site or tissue infection caused by microorganisms. Water-soluble inorganic compounds utilized according to the present invention that, upon dissolution elute biocidal agents such as ionic silver, can also provide valuable clinical benefit by reducing the risk of such infection.

Bone allografts, commonly implanted in spinal fusions, can be modified according to the present invention to utilize water-soluble inorganic compounds having smaller particles, preferably having average dimensions of 5 microns to 50 microns. Allograft 120, illustrated schematically in FIG. 7, includes cancellous bone 122 defining interstices 124 and external surface irregularities carrying water-soluble inorganic particles 126, again shown as open circles for simplicity, according to the present invention. As described above in relation to FIG. 5B, it is preferable to only partially fill interstices 124 when flexibility or compressibility of the implant is desired during implantation. One example of a compressible allograft is OsteoSponge™ bone matrix available from Bacterin International, Inc., Belgrade, Mont.

Spinal fusion, for which allograft 120 may be utilized, is a surgical technique used to fuse two or more vertebrae together. This procedure is used primarily to eliminate pain caused by the motion of degenerating vertebrae by immobilizing the vertebrae itself. There are several types spinal fusion procedures including posterolateral fusion and interbody fusion; both procedures utilize bone allograft material to aide in fusing together adjoining vertebrae. In most procedures bone fusion is augmented by the use of metallic screws, rods, plates or cages in order to fixate and stabilize the vertebrae until such time as the bone fusion takes place, generally 6-12 months post-operatively.

Healthy bone is rich in growth factors called bone morphogenetic proteins (BMP), which naturally stimulates new bone production. Bone allografts, although denatured after acidification processing, still possess certain levels of BMP. During spinal fusion surgery disk or wedge shaped bone grafts are inserted between degenerative vertebrae in order to decompress the spinal column, which is often the cause of debilitating pain. These bone allograft 'spacers' are supported or fixated by the aforementioned surgical hardware. The BMP remaining within the bone allograft, as well as the growth factors in the adjacent quasi-healthy vertebrae is generally sufficient to cause the vertebrae to fuse with the inserted bone allograft. There are thirty three vertebrae within the human spinal column. Fusing two or more such vertebrae together does have a patient motion limiting effect, however this limitation is preferred over the debilitating pain of degenerative bone disease.

Spinal fusion allografts are generally machined to specific sizes, shapes and designs to afford proper function, insertion and fixation within the surgical procedure. Being fabricated from human bone, such material generally is composed of both cortical (compact and dense) and cancellous (spongy and porous) bone, also referred to as trabecular bone. Cancellous bone has a large-pore honeycombed structure with an average pore size ranging from 100 microns to 600 microns, depending on the specific tissue. It is this type and size of porosity that porous metal coatings for orthopedic implants are modelled after. Consequently, the present inventor recognizes that bone allografts composed partially or completely of cancellous bone have an intrinsic porous structure affording the inclusion of small particle, preferably 5 microns to 50 microns in average size, water-soluble inorganic compounds that possess osteoinductive and/or antimicrobial properties. Such particles can be impregnated into the spongy, porosity of cancellous bone with the aid of diluents and/or surfactants, which lower surface tension, if necessary. The particles can be fixed within the cancellous porosity, if necessary by the use of biocompatible adhesives or polymers; such polymers include polysaccharides (such as chitosan, alginate, and gylcosaminoglycans), poly-α-hydroxy acids (such as PLA and PGA), polyethylene glycol (PEG) and amino acids.

Although, as previously referenced, processed bone allograft material maintains some of it original BMP growth factors, it is important to recognize that BMP levels are nonetheless degraded by the acidification process associated with cleaning and preparing of the cadaveric bone prior to fabrication. Therefore an osteoinductive water-soluble inorganic compound impregnated into the interstices of porous cancellous bone can only improve the osseostimulative signalling that transpires upon dissolution of the inorganic particles.

Additionally there are other cancellous-related allograft materials, such as OsteoSponge™, from Bacterin International, Inc. whose bone acidification process also decalcifies the bone to such an extent that the allograft becomes 'spongy', allowing it to be compressed and squeezed into gaps or spaces in bone. Such bony spaces are often caused by the surgical removal of bone tumors or can be intentionally created to accommodate the design of implants, such as interbody spinal fusion cages. In either case, the intent of the placement of the spongy allograft is to encourage new bone to growth within the porous cancellous spongy structure aided by the inherent BMP growth factors within the allograft. In such applications, partially filling the cancellous voids of spongy bone allografts with adherent osteoinductive water-soluble inorganic particles according to the present invention maintains the compression benefits of the allograft, while affording enhanced osteoinductive signalling and bone ingrowth.

Any transplantation of allograft material runs the risk of infection, be it transmitted via donor or introduced operatively, at the time of surgery. A surgical site infection from tissue transplantation, from whatever its source, is a most unwelcomed complication, having serious associated patient morbidity and mortality risks, as well as significant interventional therapy costs. Therefore antimicrobial water-soluble inorganic compound particles utilized according to the present invention to release biocidal agents, such as ionic silver, if infused or otherwise impregnated within the cancellous bone matrix of allografts provides beneficial antimicrobial prophylaxis.

Lastly, employing larger osteoinductive water-soluble inorganic particles, in the range of 100 microns to 800 microns, into softer tissue, like ligaments and tendons, according to the present invention can provide the opportunity for improved or accelerated bone attachment to said tissue, by osteoinductive signalling upon dissolution of said particles. Also, as these large osteoinductive particles dissolve, pores within the tissue will be generated, affording voids for bone infiltration, matrix deposition and attachment. Non-antibiotic antimicrobial water-soluble inorganic compounds of similar size and range can also be utilized in softer tissue according to the present invention. Here the allograft itself provides the requisite growth factors or stimuli, while the dissolution of the antimicrobial water-soluble inorganic particles simultaneously creates both voids for bone ingrowth and antimicrobial prophylaxis. Combining both osteoinductive and antimicrobial water-soluble inorganic particles, separately or combined within a single formulated inorganic compound, provides additional clinical benefits.

In the example of a ligament allograft, much like the aforementioned L-C Ligament™ by Soft Tissue Repair, Inc., the distal and proximal ends of the ligament allograft can be infused or injected, again with the aid of diluents and/or surfactants, with osteoinductive and, if so desired, antimicrobial, water-soluble inorganic particles of suitable size to induce a more rapid and secure bone ingrowth at the bone/ligament interface. Likewise the ligamentous portion of the allograft can be infused or injected in a similar fashion with antimicrobial water-soluble inorganic particles to provide only antimicrobial prophylaxis to the ligamentous portion of the allograft. In this manner, upon particle dissolution, one provides ionic osteoinductive stimuli at the ligament/bone attachment interface, while providing antimicrobial ligament prophylaxis across the entire ligament allograft.

Although specific features of the present invention are shown in some drawings and not in others, this is for convenience only as each feature may be combined with any or all of the other features in accordance with the invention. While there have been shown, described, and pointed out fundamental novel features of the present invention as applied to one or more preferred embodiments thereof, it will be understood that various omissions, substitutions, and changes in the form and details of the compositions and devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature.

It is the intention, therefore, to be limited only as indicated by the scope of the claims appended hereto. Other embodiments will occur to those skilled in the art and are within the following claims.

What is claimed is:

1. A method for controlling generation of biologically desirable voids in a composition placed in proximity to tissue in a patient, comprising:
   selecting at least one water-soluble inorganic material capable of resisting degradation when subjected to sterilization temperatures, remaining water soluble and biologically functional after being subjected to sterilization temperatures, having at least one sintering temperature and having at least a first average particle dimension and a desired dissolution rate;
   selecting a poorly-water-soluble matrix material having a physically continuous interconnected matrix as a porous structure disposed on at least a portion of the outer surface of an implant and defining interstices within the porous structure, wherein the first average particle dimension is selected to be smaller than the average dimension of the interstices;
   blending the water-soluble inorganic material within at least some of the interstices of the porous structure;
   attaching the water-soluble inorganic material within the interstices to form the composition on the implant, the attaching including heating to the at least one sintering temperature; and
   placing the implant carrying the composition into the patient in proximity to tissue so that the water-soluble inorganic material progressively dissolves at a predetermined rate to generate biologically desirable voids by gradually exposing more of the interstices into which tissue can then grow to assist fixation of the implant within the patient.

2. The method of claim 1 wherein at least a majority of the water-soluble inorganic material is particles having dimensions averaging below 100 microns.

3. The method of claim 2 wherein the interstices have average dimensions ranging from greater than 100 microns to about 1000 microns.

4. The method of claim 2 wherein the water-soluble inorganic material includes at least one water-soluble glass.

5. The method of claim 4 wherein the water-soluble glass includes at least one osteoinductive constituent.

6. The method of claim 4 wherein at least some of the water-soluble glass includes a minimum effective concentration of at least one non-antibiotic antimicrobial agent to have a biocidal effect on at least one targeted pathogenic microorganism.

7. The method of claim 6 wherein the antimicrobial agent includes a metal that is releasable in ionic form.

8. The method of claim 7 wherein the metal includes silver that is releasable as silver ions.

9. The method of claim 6 wherein the water-soluble inorganic material further includes at least one constituent having osteoinductive properties.

10. The method of claim 9 wherein the water-soluble glass is bioactive.

11. The method of claim 6 wherein the water-soluble glass is bioactive.

12. The method of claim 6 wherein the water-soluble glass has at least osteoinductive properties.

13. The method of claim 4 wherein the water-soluble glass is bioactive.

14. The method of claim 4 wherein the water-soluble glass has at least osteoinductive properties.

15. The method of claim 1 wherein attaching includes heating the blended material to fix the water-soluble inorganic materials within the interstices.

16. The method of claim 1 wherein the poorly-water-soluble matrix material includes particles of at least one of hydroxyapatite, tricalcium phosphate and biphasic calcium phosphate.

17. The method of claim 1 wherein the implant is metallic and the poorly-water-soluble matrix material includes metallic particles affixed to at least a portion of the outer surface of the metallic implant.

18. The method of claim 17 wherein the metallic implant is a fixation device having a shaft and having threads on a threaded region for engaging bone, and the composition is disposed about at least the threaded region.

19. The method of claim 18 further including placing water-soluble inorganic material containing at least one non-antibiotic antimicrobial agent about at least a portion of the shaft.

20. The method of claim 18 wherein the fixation device is an external fixator device.

21. The method of claim 18 wherein the composition includes water-soluble glass having at least osteoinductive properties.

22. The method of claim 17 wherein the metallic implant is a component of an artificial joint.

23. The method of claim 22 wherein the composition includes water-soluble glass having at least osteoinductive properties.

24. The method of claim 1 wherein at least a majority of the water-soluble inorganic material is particles having dimensions between about 10 microns to about 50 microns.

25. The method of claim 1 wherein the water-soluble inorganic material includes particles having at least first and second formulations which have different rates of dissolution.

26. The method of claim 1 wherein some of the water-soluble inorganic material includes at least a first concentration of a non-antibiotic antimicrobial agent and other of the water-soluble inorganic material includes at least a second concentration of the antimicrobial agent that is different from the first concentration.

27. The method of claim 1 wherein the water-soluble inorganic material is selected to have at least two different average particle dimensions.

28. The method of claim 1 wherein the water-soluble inorganic material includes at least one water-soluble glass.

29. The method of claim 28 wherein the water-soluble glass is bioactive.

30. The method of claim 28 wherein the water-soluble glass has at least osteoinductive properties.

31. The method of claim 1 wherein the implant is metallic and the poorly-soluble matrix material includes at least one of a porous surface, an etched surface, and a roughened surface.

32. The method of claim 1 further including mixing the water-soluble inorganic material with at least one constituent that alters the hydrophilicity of the mixture to change the rate of water absorption of the water-soluble inorganic material.

33. The method of claim 32 wherein the at least one constituent also assists in attaching the water-soluble inorganic material within the interstices.

34. The method of claim 33 wherein the at least one constituent is biodegradable.

35. The method of claim 1 wherein substantially only particles of water-soluble inorganic material are selected to be blended within the interstices of the porous structure.

36. The method of claim 35 wherein at least some of the particles are bioactive inorganic compounds.

37. The method of claim 1 wherein the water-soluble inorganic material remains therapeutically effective after withstanding temperatures in excess of 400 degrees Celsius.

38. The method of claim 1 wherein the water-soluble inorganic material consists essentially of at least one type of water-soluble glass.

39. The method of claim 1 wherein the water-soluble inorganic material consists essentially of at least one type of bioactive glass.

40. The method of claim 1 further including sterilizing the composition after the water-soluble inorganic material is attached within the interstices and before the composition is placed into the patient.

41. The method of claim 1 including generating biologically desirable voids having an average cross-sectional dimension greater than 100 microns.

42. A method for controlling generation of biologically desirable voids in a composition placed in proximity to tissue in a patient, comprising:
selecting at least one water-soluble inorganic material having at least a first average particle dimension and a desired dissolution rate;
selecting a poorly-water-soluble matrix material having a physically continuous interconnected matrix as a porous structure disposed on at least a portion of the outer surface of an implant and defining interstices within the porous structure, wherein the first average particle dimension is selected to be smaller than the average dimension of the interstices;
blending the water-soluble inorganic material within at least some of the interstices of the porous structure;
attaching the water-soluble inorganic material within the interstices by sintering the water-insoluble inorganic material to the matrix material to form the composition on the implant; and
placing the implant carrying the composition into the patient in proximity to tissue so that the water-soluble inorganic material progressively dissolves at a predetermined rate to generate biologically desirable voids by gradually exposing more of the interstices into which tissue can then grow to assist fixation of the implant within the patient.

43. The method of claim 42 wherein the at least one water-soluble inorganic material is capable of resisting degradation when subjected to sterilization temperatures and remains water soluble and biologically functional after being subjected to sterilization temperatures.

44. The method of claim 42 including generating biologically desirable voids having an average cross-sectional dimension greater than 100 microns.

45. A method for controlling generation of biologically desirable voids in a composition placed in proximity to tissue in a patient, comprising:
selecting at least one water-soluble inorganic material capable of resisting degradation when subjected to sterilization temperatures, remaining water soluble and biologically functional after being subjected to sterilization temperatures including remaining therapeutically effective after withstanding temperatures in excess of 400 degrees Celsius, and having at least a first average particle dimension and a desired dissolution rate;
selecting a poorly-water-soluble matrix material having a physically continuous interconnected matrix as a porous structure disposed on at least a portion of the outer surface of an implant and defining interstices within the porous structure, wherein the first average particle dimension is selected to be smaller than the average dimension of the interstices;
blending the water-soluble inorganic material within at least some of the interstices of the porous structure;
attaching the water-soluble inorganic material within the interstices to form the composition on the implant, the attaching including heating to a temperature in excess of 400 degrees Celsius; and
placing the implant carrying the composition into the patient in proximity to tissue so that the water-soluble inorganic material progressively dissolves at a predetermined rate to generate biologically desirable voids by gradually exposing more of the interstices into which tissue can then grow to assist fixation of the implant within the patient.

\* \* \* \* \*